United States Patent [19]

Sih

[11] 4,256,667

[45] Mar. 17, 1981

[54] 2-DECARBOXY-2-AMINOMETHYL-19-HYDROXY-19-METHYL-6a-CARBA-PGI$_2$ COMPOUNDS

[75] Inventor: John C. Sih, Portage, Mich.

[73] Assignee: The Upjohn Company, Kalamazoo, Mich.

[21] Appl. No.: 126,464

[22] Filed: Mar. 3, 1980

Related U.S. Application Data

[62] Division of Ser. No. 54,720, Jul. 5, 1979, Pat. No. 4,225,507.

[51] Int. Cl.$^3$ .................. C07C 87/34; C07C 87/40; C07C 87/451; C07C 87/453
[52] U.S. Cl. .................. 564/384; 564/428; 564/453; 564/454; 564/460
[58] Field of Search .............. 260/563 P, 563 R, 571, 260/573, 574, 570.9

[56] References Cited

U.S. PATENT DOCUMENTS

| | | | |
|---|---|---|---|
| 3,849,474 | 11/1974 | Abraham et al. | 260/584 A X |
| 3,919,285 | 11/1975 | Axen | 560/121 |
| 3,935,240 | 1/1976 | Mallion | 260/571 X |
| 3,954,741 | 5/1976 | Schaaf et al. | 260/561 R X |
| 4,064,351 | 12/1977 | Sukai et al. | 260/574 X |

FOREIGN PATENT DOCUMENTS 2635985  2/1978  Fed. Rep. of Germany ........... 560/121

OTHER PUBLICATIONS

Johnson, "Jacs", 100, pp. 7690–7704, (1978).

*Primary Examiner*—John Doll
*Attorney, Agent, or Firm*—Robert A. Armitage

[57] ABSTRACT

The present invention provides novel 2-decarboxy-2-aminomethyl-19-hydroxy-19-methyl-6a-carba-PGI$_1$ compounds which are useful for pharmacological purposes, e.g., anti-asthmatic indications.

1 Claim, No Drawings

2-DECARBOXY-2-AMINOMETHYL-19-HYDROXY-19-METHYL-6A-CARBA-PGI₂ COMPOUNDS

DESCRIPTION

CROSS REFERENCE TO RELATED APPLICATION

The present invention is a divisional application of U.S. Ser. No. 054,720, filed July 5, 1979, now U.S. Pat. No. 4,225,507.

BACKGROUND OF THE INVENTION

The present invention provides novel prostacyclin analogs. Particularly, the present invention relates to prostacyclin analogs substituted at the C-19 position by hydroxy.

Particularly, the present invention relates to 2-decarboxy-2-aminomethyl-19-hydroxy-19-methyl-6a-carba-PGI₂ compounds. The novel prostacyclin analogs are useful for pharmacological purposes, e.g., as anti-asthmatic agents. The preparation and use of these compounds is incorporated here by reference from U.S. Pat. No. 4,225,507.

PRIOR ART

For background on prostacyclin, see for example R. A. Johnson, et al., Prostaglandins 12, 915–928 (1976) and R. A. Johnson, et al., J. Am. Chem. Soc. 100, 7690–7704 (1978), and, as to pharmacological activity, the references cited therein. For analogs of prostacyclin, see, for example, J. Fried, et al., Proc. Natl. Acad. Sci. U.S.A. 74, 2199–2203, K. C. Nicolaou, et al., J.C.S. Chem. Comm. 1977, 331–332, N. A. Nelson, J. Am. Chem. Soc. 99, 7362–7363 (1977), and K. Kojima, et al., Tetra. Letters, 1978, (1977), and K. Kojima, et al., Tetra. Letters, 1978, 3743–3746. Regarding the nomenclature for analogs of PGI₂, see R. A. Johnson, et al., Prostaglandins 15, 737–740 (1978).

SUMMARY OF THE INVENTION

The present invention particularly provides a prostacyclin-type compound of the formula

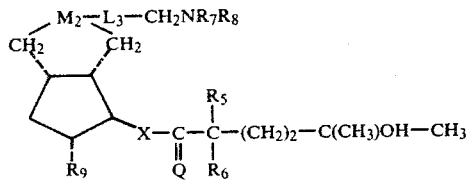

wherein L₃ is
(1) —(CH₂)$_n$—, wherein n is one to 5, inclusive,
(2) —(CH₂)$_p$—CF₂—, wherein p is 2, 3, or 4, or
(3) —CH₂—CH=CH—;
wherein M₂ is

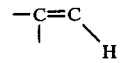

wherein Q is oxo, α-H:β-H, α-OH:β-R₄, or α-R₄:β-OH,
wherein R₄ is hydrogen or alkyl of one to 4 carbon atoms, inclusive,
wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro;
wherein R₇ and R₈ are hydrogen, alkyl of one to 12 carbon atoms, inclusive, benzyl, or phenyl, being the same or different; wherein R₉ is hydrogen or hydroxyl; and wherein X is
(1) trans—CH=CH—,
(2) cis—CH=CH—,
(3) —C≡C—, or
(4) —CH₂CH₁—.

I claim:
1. A prostacyclin-type compound of the formula

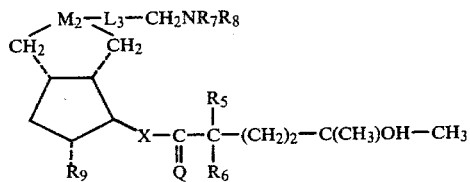

wherein L₃ is
(1) —(CH₂)$_n$—, wherein n is one to 5, inclusive,
(2) —(CH₂)$_p$—CF₂—, wherein p is 2,3, or 4, or
(3) —CH₂—CH=CH—;
wherein M₂ is

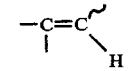

wherein Q is oxo, α-H:β-H, α-OH:β-R₄, or α-R₄:β-OH,
wherein R₄ is hydrogen or alkyl of one to 4 carbon atoms, inclusive,
wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro;
wherein R₇ and R₈ are hydrogen, alkyl of one to 12 carbon atoms, inclusive, benzyl, or phenyl, being the same or different; wherein R₉ is hydrogen or hydroxyl; and wherein X is
(1) trans—CH=CH—,
(2) cis—CH=CH—,
(3) —C≡C—, or
(4) —CH₂CH₂—.

* * * * *

UNITED STATES PATENT OFFICE
CERTIFICATE OF CORRECTION

Patent No. 4,256,667        Dated    17 March 1981

Inventor(s)  John C. Sih

It is certified that error appears in the above-identified patent and that said Letters Patent are hereby corrected as shown below:

Column 2, lines 1-6, "$-\underset{\underset{H}{|}}{C}=C$" should read -- $-\underset{|}{C}=C\underset{H}{\sim}$ --;

line 21, "$-CH_2CH_1-$" should read -- $-CH_2CH_2-$ --.

*Signed and Sealed this*

*Second* Day of *June 1981*

[SEAL]

Attest:

RENE D. TEGTMEYER

*Attesting Officer*    *Acting Commissioner of Patents and Trademarks*